United States Patent [19]
Roth et al.

[11] Patent Number: 5,810,877
[45] Date of Patent: *Sep. 22, 1998

[54] ENDOSCOPIC MICROSURGICAL INSTRUMENTS AND METHODS

[75] Inventors: Alex T. Roth, Redwood City; Scott H. Miller, Sunnyvale, both of Calif.

[73] Assignee: Heartport, Inc., Redwood City, Calif.

[*] Notice: The term of this patent shall not extend beyond the expiration date of Pat. No. 5,501,698.

[21] Appl. No.: 744,208

[22] Filed: Nov. 5, 1996

Related U.S. Application Data

[60] Continuation of Ser. No. 560,441, Nov. 17, 1995, Pat. No. 5,618,306, which is a division of Ser. No. 194,946, Feb. 14, 1994, Pat. No. 5,501,698.

[51] Int. Cl.$^6$ ................................................ A61B 17/00
[52] U.S. Cl. ........................................ 606/205; 606/174
[58] Field of Search .................................. 606/205, 206, 606/207, 208, 174, 170

[56] References Cited

U.S. PATENT DOCUMENTS

| | | |
|---|---|---|
| 3,404,677 | 10/1968 | Springer . |
| 4,258,716 | 3/1981 | Sutherland . |
| 4,433,687 | 2/1984 | Burke et al. . |
| 4,462,404 | 7/1984 | Schwarz et al. . |
| 4,643,190 | 2/1987 | Heimberger . |
| 4,644,651 | 2/1987 | Jacobsen . |
| 4,760,848 | 8/1988 | Hasson . |
| 4,955,887 | 9/1990 | Zirm . |
| 5,133,735 | 7/1992 | Slater et al. . |

(List continued on next page.)

OTHER PUBLICATIONS

Product Brochure—Buhler–ErgonoMIC—System, GmbH, Mehlbeerenstrasse 2, D–8028 Taufkirchen, Germany.
Product Brochure—Suturing, Columbia Presbyterian Hospital, NY, New York, and Motreal Medical Center, Tuucker, Georgia.
Product Brochure—Szabo–Beroi Needle Driver Set, STORZ, Karl Storz Endoscopy, Apr. 1993.
Product Brochure—"The ultimate" laparoscopic Needle Holder, WJ Medical.
Product Brochure—The Surgical Armamentarium, V. Mueller, Baxter, 1988.
Acufex Rotary Graspers, Acufex Microsurgical, Inc., Catalog, 1982.
Product Brochure—Dekalb Laparoscopic Instruments, Endotec, Endoscopic Technologies, Inc.
Product Brochure—Surgical Instruments, Stille®, 1993.
Product Brochure, Hermann Dausch—Fabrik Chirurgischer Instrumente, Bahnhofstrasse 76, D–7200 Tuttlingen, Germany.

*Primary Examiner*—Michael Buiz
*Assistant Examiner*—Kevin Truong
*Attorney, Agent, or Firm*—Jeffry J. Grainger; Jens E. Hoekendijk; Michael J. Lynch

[57] ABSTRACT

The invention provides devices and method for performing extremely small-scale, minimally-invasive microsurgery such as thoracoscopic coronary artery bypass grafting. The instruments of the invention utilize a symmetrical, forcep-like actuator which provides extremely precise actuation and control of the instrument and which mimics the feel of instruments used in conventional open surgical procedures. The instruments generally include a pair of coaxially arranged shafts, an end-effect at the distal ends of the shafts, and an actuator at the proximal ends of the shafts. The actuator includes a pair of arms pivotally coupled to one of either the outer or inner shaft, and a pair of links pivotally coupled at one end to the arms, and at a second end to the other of the shafts. The links are coupled to a proximal portion of the arms to maximize mechanical advantage and reduce interference. The actuator may be easily adapted for either pull-type or push-type actuation, and for either outer shaft or inner shaft translation. The end-effectors may have a variety of configurations, including needle drivers, forceps, scissors, and clip appliers.

20 Claims, 12 Drawing Sheets

U.S. PATENT DOCUMENTS

| | | |
|---|---|---|
| 5,152,780 | 10/1992 | Honkanen et al. . |
| 5,171,256 | 12/1992 | Smith et al. . |
| 5,174,300 | 12/1992 | Bales et al. . |
| 5,192,298 | 3/1993 | Smith et al. . |
| 5,219,357 | 6/1993 | Honkanen et al. . |
| 5,234,453 | 8/1993 | Smith et al. . |
| 5,308,357 | 5/1994 | Lichtman . |
| 5,370,658 | 12/1994 | Scheller et al. . |
| 5,439,468 | 8/1995 | Schulze et al. . |
| 5,498,256 | 3/1996 | Furnish . |
| 5,501,698 | 3/1996 | Roth et al. ............................. 606/205 |

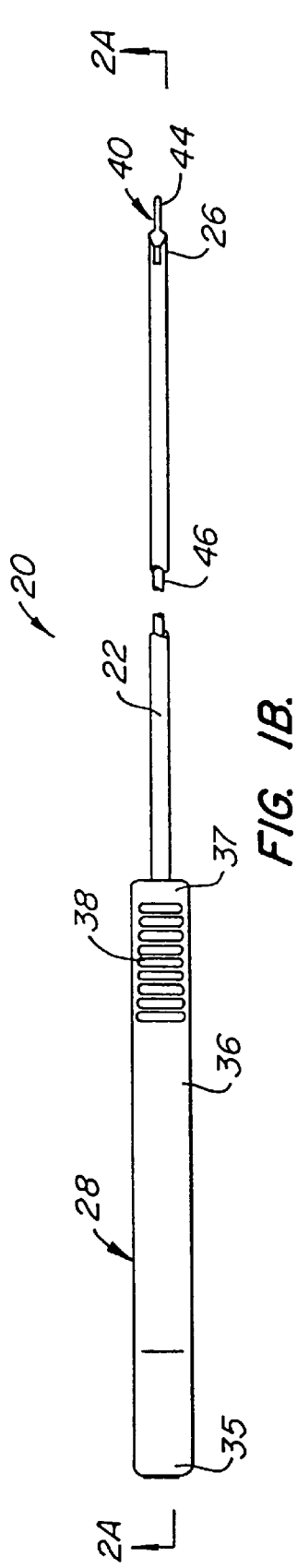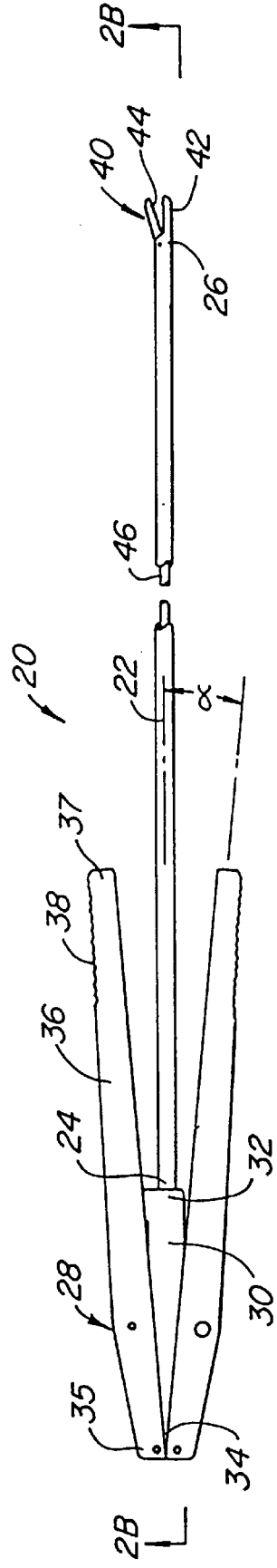

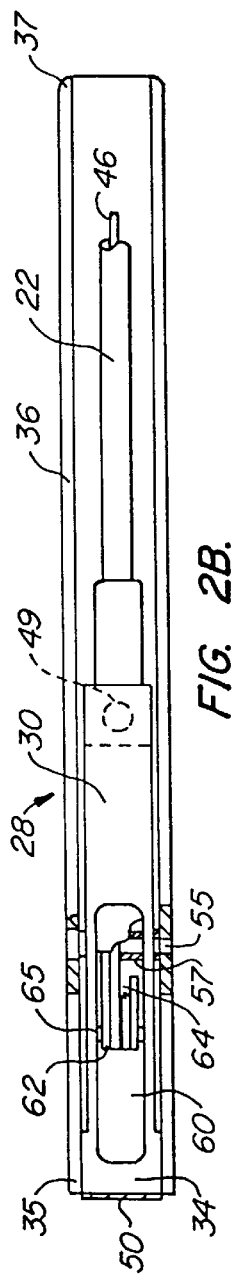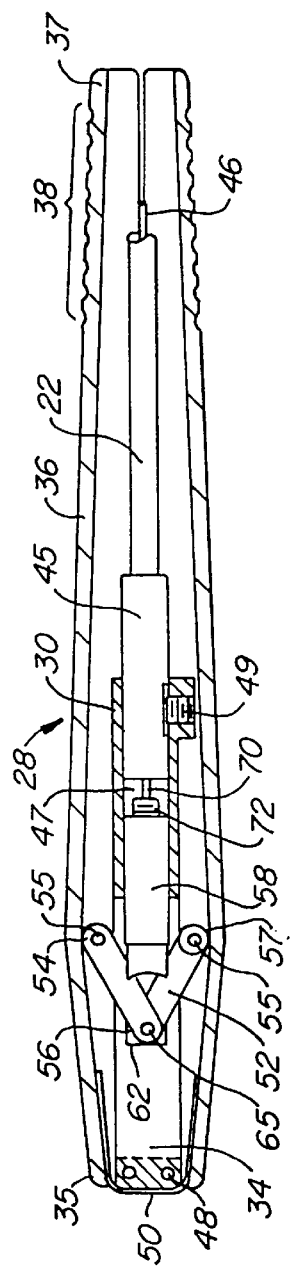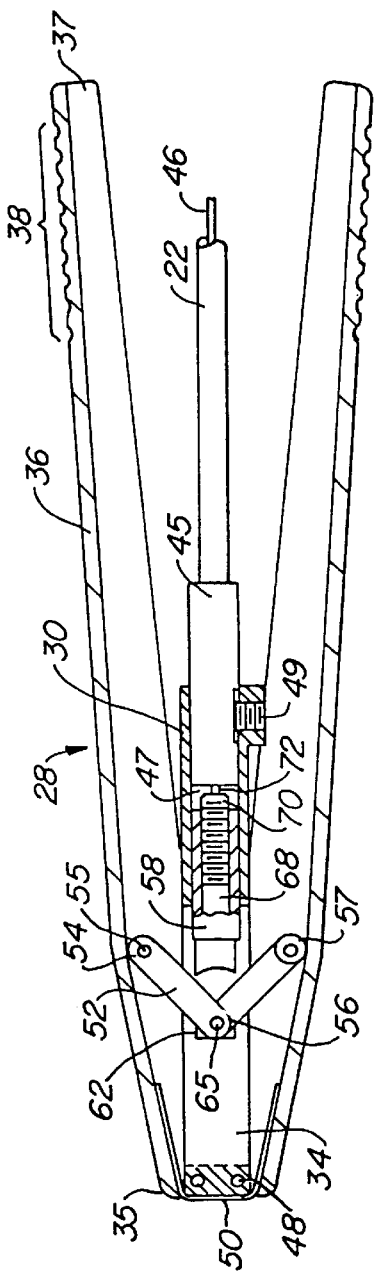

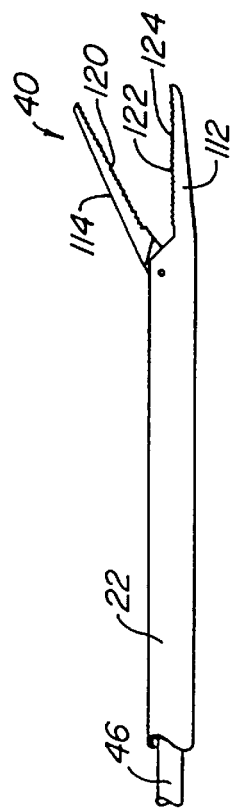
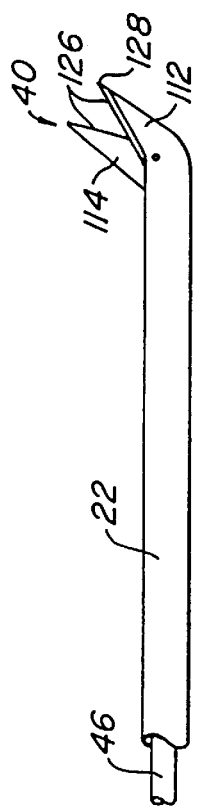
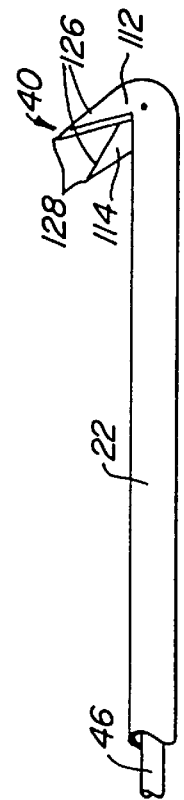
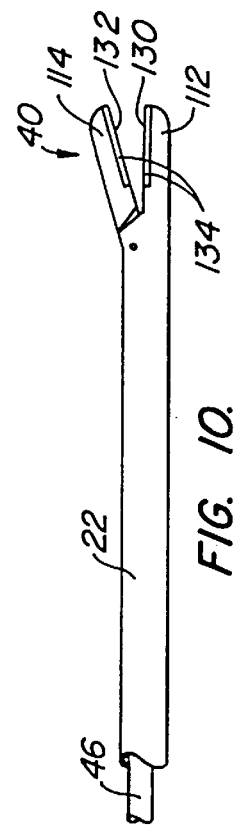
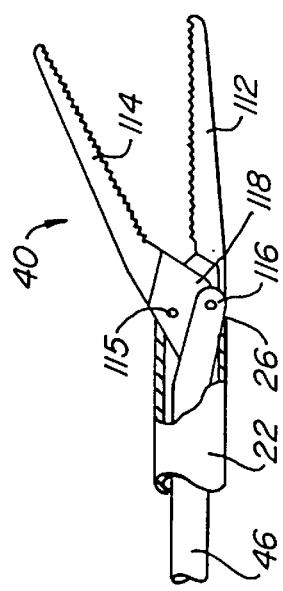
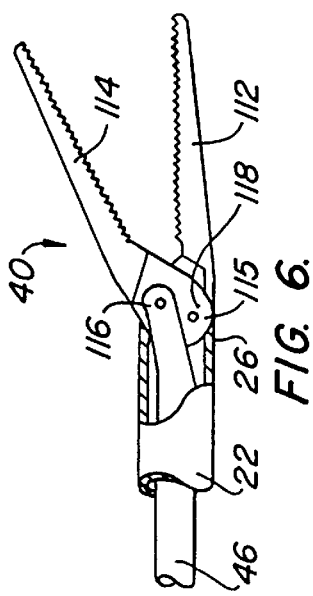
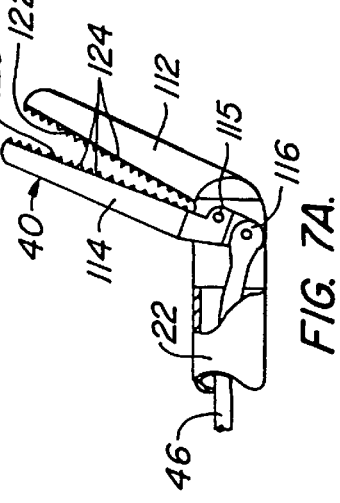

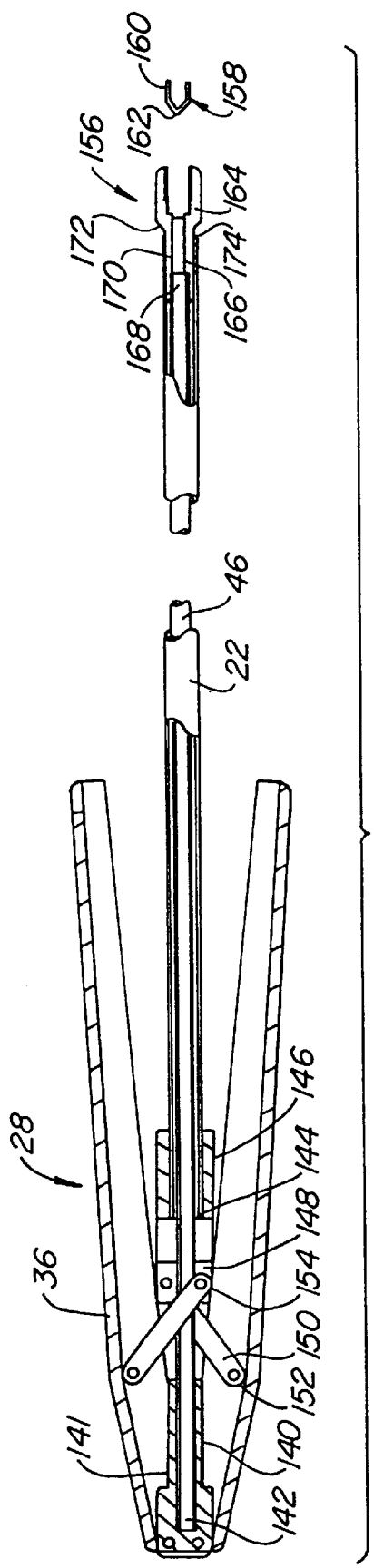
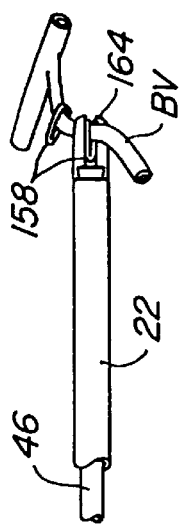
FIG. 11.
FIG. 12.

ENDOSCOPIC MICROSURGICAL INSTRUMENTS AND METHODS

This is a Continuation of application Ser. No. 08/560,441 filed Nov. 17, 1995, now U.S. Pat. No. 5,618,306 which is a division of Ser. No. 08/194,946, filed Feb. 14, 1994, now U.S. Pat. No. 5,501,698.

FIELD OF THE INVENTION

This invention relates generally to instruments for performing minimally-invasive surgery, and more specifically, to instruments for performing extremely small-scale, minimally-invasive microsurgeries such as coronary artery bypass grafting.

BACKGROUND OF THE INVENTION

Minimally-invasive surgical techniques, such as thoracoscopy, laparoscopy, pelviscopy, endoscopy, and arthroscopy, minimize patient trauma by providing access to interior body cavities through very small incisions or through percutaneous cannulas known as trocar sleeves. To perform a surgical procedure, elongated, low-profile instruments are introduced into a body cavity through these incisions or trocar sleeves. Visualization is facilitated by percutaneous visualization devices known as laparoscopes, endoscopes, arthroscopes, and the like, which typically consist of a video camera configured for introduction through a small incision or trocar sleeve to allow observation of the body cavity on a video monitor. By obviating the need for a large, open incision to expose the body cavity, minimally-invasive techniques can significantly reduce the pain, recovery period, morbidity and mortality rates, and cost of open surgical procedures without a sacrifice in efficacy.

In recent years, minimally-invasive techniques have been developed to facilitate the performance of a variety of surgical procedures on organs and ducts of the abdominal and pelvic cavities. Well-known examples of such procedures include laparoscopic cholecystectomy, laparoscopic appendectomy, laparoscopic hysterectomy, and laparoscopic hernia repair.

A particularly important milestone in minimally-invasive surgery has been attained with the development of thoracoscopic techniques for surgery of the heart and great vessels. Such techniques are described in co-pending, commonly-assigned U.S. patent application Ser. No. 08/023,778, filed Feb. 22, 1993, now U.S. Pat. No. 5,452,733, the complete disclosure of which is hereby incorporated herein by reference. In that application, thoracoscopic techniques for performing coronary artery bypass grafting (CABG) are described which eliminate the need for the sternotomy or other form of gross thoracotomy required by conventional, open surgical techniques. In thoracoscopic CABG, an arterial blood source such as the internal mammary artery (IMA) is dissected from its native location, transected, and prepared for attachment to an anastomosis site on a target coronary artery, commonly the left anterior descending coronary artery (LAD). A portion of the target coronary artery containing the anastomosis site is then dissected away from the epicardium, and a small incision is made in the arterial wall. The distal end of the arterial blood source (e.g. IMA) is then anastomosed over the incision in the target coronary artery, usually by suturing. Each of these steps is performed by means of instruments introduced through small incisions or trocar sleeves positioned within intercostal spaces of the rib cage, under visualization by means of an endoscope or other percutaneous visualization device.

Because the CABG procedure requires complex microsurgery to be carried out on extremely small body structures, surgical instruments designed for laparoscopic and other minimally-invasive applications are not generally suitable for performing thoracoscopic CABG. Most laparoscopic procedures, for example, target body structures which are quite large in comparison to the coronary vessels, and do not require the high degree of precision required by microsurgeries such as CABG. Accordingly, laparoscopic instruments generally have relatively large end-effectors with relatively large ranges of movement, making such instruments ill-suited for use on very small structures like the coronary vessels. In addition, such instruments commonly have finger loops or pistol-type actuators gripped in the user's palm or between the user's thumb and forefinger, limiting the sensitivity and precision with which such instruments can be manipulated and actuated. Such finger loops or pistol-type grips also are limited to a single orientation in the user's hand and cannot be repositioned in the hand to allow better access to a body structure or to change the orientation of the end-effector.

The advent of thoracoscopic CABG and other minimally-invasive microsurgical procedures therefore demands a new generation of microsurgical instruments specifically designed to meet the unique needs of such procedures. These instruments must have a small profile for introduction through small incisions or trocar sleeves, and a length sufficient to reach the heart and other thoracic organs and vessels from various percutaneous access points. The instruments must have end-effectors adapted to perform delicate, high-precision microsurgery on very small vessels, including end-effectors having very small dimensions and very short ranges of motion. The instruments must have actuators that facilitate ergonomic, one-handed actuation with sensitivity and precision, preferably having a stroke which is large enough for comfortable actuation by the fingers and which is reduced to a very short range of motion at the end-effector. Desirably, the actuators will have a configuration which is analogous to surgical forceps or to other types of microsurgical instruments commonly utilized in open surgical procedures, shortening the learning curve required for adoption of minimally-invasive microsurgical techniques.

SUMMARY OF THE INVENTION

This invention provides instruments and methods to facilitate the performance of minimally-invasive microsurgical procedures, and particularly, the performance of thoracoscopic CABG and other procedures on the heart and great vessels. The instruments of the invention facilitate a variety of surgical activities, including application of clips or staples, suturing, incision, transection, dissection, retraction, and manipulation, and are specially adapted for use on extremely small body structures such as the coronary blood vessels. To allow precise microsurgery to be performed on a very small scale, the instruments are adapted to he held in a single hand in a manner analogous to surgical forceps. The instruments are actuated by a pair of symmetrical, proximally-hinged, forcep-like arms which can be pivoted by the fingers for sensitive and precise actuation of an end-effector. The symmetry of actuation allows each instrument to be rotated or otherwise repositioned within the user's hand to change the orientation of the end-effector without compromising the ease of actuation. Moreover, the actuator's proximal hinge, along with a proximally-disposed linkage mechanism, allow the distance between the user's hand and the body surface to be minimized for optimal control of the instrument.

In a preferred embodiment, a microsurgical instrument according to the invention comprises an outer shaft having an axial lumen, and an inner shaft slidably disposed in the axial lumen. An end-effector is coupled to the distal end of the inner shaft and is movable relative to the outer shaft. An actuator is disposed at the proximal end of the outer shaft for actuating the end-effector. The actuator includes first and second arms each coupled at its proximal end to one of either the outer shaft or the inner shaft, each arm extending distally and biased outwardly so as to form an acute angle with the outer shaft. A link is coupled to each arm and to the shaft to which the arms themselves are not coupled. In this way, the first and second arms are symmetrically pivotable so as to pivot the links, thereby translating the inner shaft relative to the outer shaft to actuate the end-effector.

The end-effector of the instrument may have a variety of configurations for performing a variety of functions. The end-effector may comprise a pair of jaws which may be adapted for various purposes, including cutting, grasping, holding a suture needle, and applying a clip or staple. In an exemplary embodiment, the end-effector comprises a first jaw fixed to the outer shaft, and a second jaw coupled to the inner shaft, such that translating the inner shaft relative to the outer shaft moves the second jaw relative to the first jaw. The second jaw may be pivotable, axially slidable, rotatable, or deflectable relative to the first jaw. The jaws may be configured to have opposing gripping surfaces for grasping tissue or holding a suture needle, or may have sharp cutting edges movable in a shearing relationship relative to each other for cutting tissue. The jaws may further be disposed at various angles and orientations relative to the inner and outer shafts to provide a range of end-effector configurations to meet a variety of surgical needs.

Alternatively, the end-effector may be adapted for applying a clip or staple to a body structure. In an exemplary configuration, the end-effector includes a pair of jaws fixed to tile distal end of the inner shaft and adapted to hold a clip or staple between them. The jaws are biased away from each other and are deflectable toward one another. Upon actuation, the outer shaft is configured to slide distally over a proximal portion of the jaws so as to urge the jaws toward one another, thereby closing the clip or staple.

Preferably, the instruments of the invention are adapted for extremely small scale microsurgical procedures such as coronary anastomosis. To facilitate such procedures, the arms of the actuator are configured to provide a comfortable range of motion for forcep-like finger actuation, a range of motion which is reduced to a very small range of motion at the end-effector, thereby providing sensitive and precise actuation for very small end-effector movements.

In actuating very small end-effectors through very small ranges of motion, the minimization of friction is important in providing smooth and precise actuation. To reduce friction, the links are coupled to the shaft (either inner or outer) such that the transverse force exerted on the shaft by one link is opposed by a transverse force exerted on the shaft by the other link. Usually, this is accomplished by coupling the inner ends of the links to the shaft at points which are equidistant from the proximal end of the shalt. In this way, as the arms are pivoted inwardly, the links do not urge the inner shaft against the outer shaft (or vice versa), which would produce friction as the shafts move relative to each other.

The arms may be bendable or rigid, and the arms may be coupled to the inner or outer shaft in various ways, including by pins, by living hinges, by bar linkages, or by other means.

Preferably, however, the arms arc hinged at their proximal ends to the inner or outer shaft. A means for biasing the arms outward is provided, which in one embodiment comprises a flat spring coupled to each arm. With a hinge arrangement, the arms may be rigid, rather than being bendable or resilient, permitting a wide variety of materials, and geometries to be used. In this way, the arms may be designed for optimum performance and minimum cost.

The links may be configured so as to translate the inner shaft either distally or proximally relative to the outer shaft as the arms are pivoted inwardly. To provide translation of the inner shaft proximally, the inner ends of the links are disposed proximal to the outer ends of the links. To provide translation of the inner shaft distally, the inner ends of the links are disposed distal to the outer ends of the links.

The instruments of the invention are further advantageous in that they allow the user to hold and actuate the instrument from a position which is as close as possible to the surface of the patient's body, optimizing control of the instrument. The proximally-hinged arms permit the user to engage the arms near their distal ends, and to introduce the instrument into the patient's body cavity through an incision or trocar sleeve up to the distal ends of the arms. In this way, the user may engage and manipulate the instrument in a position immediately adjacent the surface of the patient's body. The links are preferably coupled to the arms in a proximal portion thereof so as not to interfere with or limit introduction of the instrument. Proximal disposition of the links also maximizes the mechanical advantage obtained from the forces exerted on the distal ends of the arms, and allows the stroke of the arms to be amplified relative to the range of motion of the end-effector.

The invention may further include means for locking the arms in a closed position. This may be useful to ensure the jaws of the end-effector are closed for introduction or removal from the body cavity, or to reduce the risk of inadvertent injury to the patient caused by an open end-effector.

Usually, the instruments of the invention are adapted for endoscopic uses, wherein the end-effector is introduced though a small incision or trocar sleeve into the body cavity. To facilitate such introduction, the profile of the end-effector and outer shaft are preferably minimized. In one embodiment, the outer shaft has a diameter of less than about 5 mm.

The instruments of the invention may be utilized to perform a variety of surgical procedures, both conventional, open) procedures and minimally-invasive procedures. In an endoscopic method of treatment according to the invention, the distal end of the instrument is introduced through a percutaneous penetration into a body cavity, and, under visualization by means of a scope introduced through a percutaneous penetration, a distal portion of at least one arm is pressed inwardly to symmetrically pivot both arms toward the shaft, thereby closing the jaws of the end-effector on a body structure in the body cavity. In various embodiments, the method may be used for cutting, dissecting, transecting, retracting, or otherwise manipulating a body structure, as well as for suturing, or for applying clips or staples to a body structure. In a particularly preferred embodiment, the method is utilized in a thoracoscopic CABG procedure for dissecting a graft vessel such as the IMA from its native location, and performing an anastomosis of the graft vessel to a coronary artery such as the LAD.

A further understanding of the nature and advantages of the invention may be realized by reference to the remaining portions of the specification and the drawings.

BRIEF DESCRIPTION OF THE DRAWINGS

FIG. 1A–1B are side and top elevational views, respectively, of a microsurgical instrument constructed in accordance with the principles of the invention.

FIGS. 2A–2B are side and top cross-sectional views, respectively, of a first embodiment of an actuator in the microsurgical instrument of FIG. 1.

FIG. 2C is a side cross-sectional view of the actuator of FIG. 2A in a closed position.

FIGS. 5–6 are side, partial cross-sectional views of two alternative embodiments of an end-effector in the microsurgical instrument of FIG. 1.

FIG. 7A is a side partial cross-section of an alternative embodiment of an end-effector in the microsurgical instrument of FIG. 1.

FIGS. 7B–10 are side elevational views of various embodiments of an end-effector in the microsurgical instrument of FIG. 1.

FIG. 11 is a side, partial cross-sectional view of a further embodiment of a microsurgical instrument constructed in accordance with the principles of the invention.

FIG. 12 is a side elevational view of a distal portion of the microsurgical instrument of FIG. 11 illustrating the application of a surgical clip to a vessel.

DETAILED DESCRIPTION OF SPECIFIC EMBODIMENTS

The instruments and methods of the invention facilitate the performance of microsurgical procedures with high precision and control. The invention is therefore useful in any procedure where very small body structures are involved or where highly-precise, very small-scale surgical maneuvers are being performed, whether conventional, open procedures or minimally-invasive procedures. Because, the instruments and methods are well-adapted for the performance of surgery through small, percutaneous incisions or trocar sleeves, the invention is particularly well-suited for the performance of minimally-invasive procedures such as thoracoscopy, laparoscopy, and pelviscopy. In a particularly preferred embodiment, for example, the instruments and methods of the invention are utilized for the performance of thoracoscopic CABG procedures, wherein specialized instruments are introduced through percutaneous penetrations and/or trocar sleeves to dissect a graft vessel such as the IMA from its native location, incise a coronary artery such as the LAD downstream of an arterial lesion, and anastomose the graft vessel to the coronary artery. No known thoracoscopic, laparoscopic, or other minimally-invasive surgical instruments are suitable for performing the ultra-precise microsurgery required in a thoracoscopic CABG procedure.

Figure 1C:
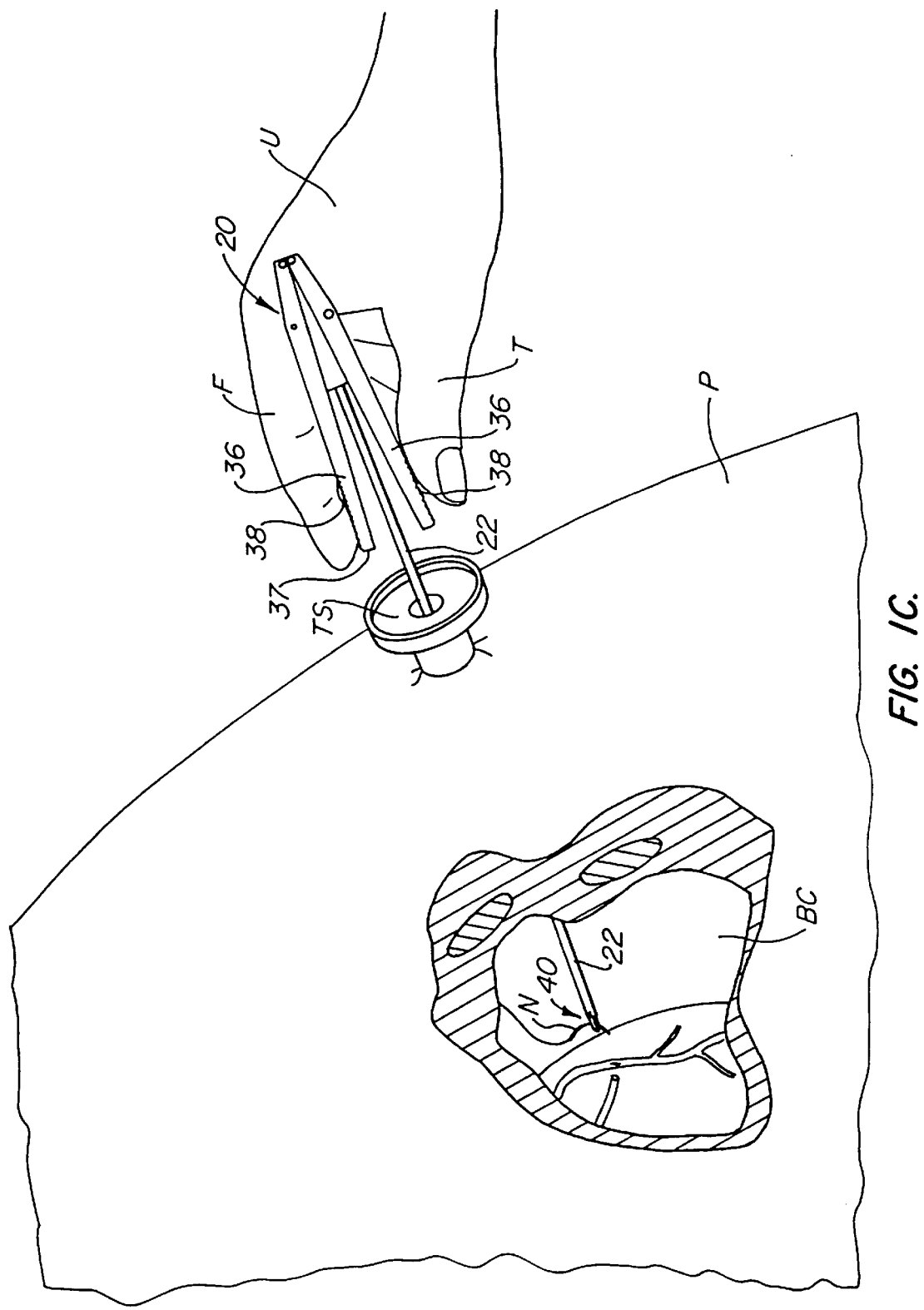
FIG. 1C is an illustration of a patient's chest in partial section illustrating the use of the instrument of FIGS. 1A–1B through a trocar sleeve.

A first preferred embodiment of a microsurgical instrument according to the invention is illustrated in FIGS. 1A–1C. Microsurgical instrument 20 includes an outer shaft 22 having a proximal end 24 and a distal end 26. Proximal end 24 of outer shaft 22 is mounted to an actuator 28. Actuator 28 includes a body 30 having a distal end 32 to which outer shaft 22 is mounted, and a proximal end 34 to which a pair of arms 36 are pivotally coupled. Arms 36 each have a proximal end 35 coupled to body 30, and a distal end 37 which is biased outwardly from outer shaft 22 to form an acute angle therewith. A finger grip 38 is disposed near the distal end 37 of each arm 36, the finger grips comprising a plurality of grooves or other textural features to facilitate gripping and actuating the instrument.

As shown in FIG. 1C, actuator 28 is configured to be held between the thumb T and index finger F of the user's hand, similar to the manner in which conventional forceps are held. Arms 36 may be engaged on finger grips 38 by the tips of finger F and thumb T, with the proximal ends 35 of arms 36 resting on the user's hand between and/or behind index finger F and thumb T. Held in this way, instrument 20 is positionable with high precision and control, and may be actuated with great ease by exerting inward pressure on finger grips 38. In an exemplary embodiment, arms 36 are 8 to 12 cm. in length, and form an angle $\alpha$ between 3° and 30°, preferably between 5° and 10°, with outer 22 in the open position.

Returning to FIGS. 1A–1B, an end-effector 40 is mounted to the distal end of outer shaft 22. End-effector 40 may have various configurations according to the function which instrument 20 is adapted to perform. In the embodiment illustrated, end-effector 40 is adapted for holding a suture needle, and includes a fixed jaw 42 mounted to outer shaft 22, and a movable jaw 44 pivotally mounted to outer shaft 22 and coupled to actuator 28 by means of an inner shaft 46, described more fully below. By pivoting arms 36 inward toward outer shaft 22, movable jaw 44 may be pivoted toward fixed jaw 42 in order to clamp a suture needle N therebetween as in FIG. 1C.

Outer shaft 22 and end-effector 40 are preferably configured for endoscopic uses, and have a profile suitable for introduction through a small percutaneous incision or trocar sleeve TS into a body cavity BC, as illustrated in FIG. 1C. Ideally, the profile (cross-sectional area) of outer shaft 22 is minimized to provide maximum clearance through an incision or trocar sleeve, thereby maximizing the maneuverability of the instrument. However, for most procedures, outer shaft 22 must have significant rigidity to resist bending or buckling. For endoscopic applications, outer shaft 22 must also have a length sufficient to reach a target site within a body cavity from a position outside of the body. In an exemplary embodiment suitable for thoracoscopic surgery on the heart, outer shaft 22 is constructed of a metal such as aluminum, titanium or stainless steel, has a round cross-section with a diameter of 2 to 10 mm, preferably about 3 to 5 mm, and has a length of about 10 to 30 cm., preferably about 20 to 25 cm.

The instruments of the invention may be configured for either pull-type or push-type actuation of end-effector 40. An exemplary embodiment of a pull-type actuator 28 is illustrated in FIGS. 2A–2C. Outer shaft 22 is fixed to a sleeve 45 retained within an axial bore 47 in body 30. A setscrew 49 engages sleeve 45 and permits axial adjustment of outer shaft 22 relative to body 30. Arms 36 are hinged to body 30 by pins 48. Means are provided for biasing arms 36 outwardly, which may comprise a flat spring 50 at the proximal end 34 of body 30 shaped so that each end of spring 50 is disposed between an arm 36 and body 30. Flat spring 50 may be a resilient, flexible metal such as stainless steel.

Various alternative means may be used for coupling arms 36 to body 30, such as a living hinge or bar linkage. Alternatively, arms 36 may be fixed to body 30 and/or to each other, and provided with sufficient flexibility to allow distal ends 37 to be deflected toward outer shaft 22. The hinge pin arrangement illustrated provides a simple and dependable coupling with the advantage that arms 36 need not be flexible, allowing a wide variety of rigid materials to be used for the arms, including metals and plastics.

A pair of links 52 each have an outer end 54 pinned to an arm 36 and an inner end 56 pinned to a cylindrical clevis 58. Outer ends 54 are coupled to arm 36 by pins 55 and bushings 57. Body 30 has an aperture 60 in which inner ends 56 of links 52 are attached to proximal end 62 of clevis 58. Proximal end 62 of clevis 58 is bifurcated by a channel 64 in which inner ends 56 of links 52 are coupled by a pin 65. Clevis 58 is slidable within axial bore 47 in body 30. A threaded hole 68 extends axially through a distal portion of clevis 58. A screw 70 is fixed to a proximal end 72 of inner shaft 46 and is threaded into hole 68, such that inner shaft 46 moves in tandem with clevis 58.

In operation, when arms 36 are pivoted toward outer shaft 22, links 52 pull clevis 58 and inner shaft 46 proximally relative to outer shaft 22, to the position shown in FIG. 2C. Releasing inward force on arms 36 allows them to return to their outward position under the force of spring 50. The outward travel of arms 36 is limited by the engagement of screw 70 and/or clevis 58 against the proximal end of sleeve 45. The extent of outward travel of arms 36, and hence the axial translation of inner shaft 46, may be adjusted by loosening setscrew 49 and axially repositioning sleeve 45.

Outer ends 54 of links 52 may be coupled to arms 36 at various positions between their proximal ends 35 and distal ends 37. In a preferred embodiment, however, outer ends 54 are coupled to arms 36 in a proximal portion thereof, preferably at a point more than ball the length of arm 36 from its distal end 37 or from finger grip 38. By maximizing the distance between the point at which the user presses on arms 36 and the point of coupling to links 52, mechanical advantage is maximized. At the same time, this proximal positioning of the links leaves open the majority of the area between the distal portion of arms 36 and outer shalt 22, eliminating any possibility of interference between links 52 and the patient's body, trocar sleeves, the user, or other objects. This is particularly useful when the instruments are introduced into the patient's body through small incisions or trocar sleeves in laparoscopic, thoracoscopic, or other minimally-invasive surgical procedures. As shown in FIG. 1C, the instruments of the invention may be introduced through such small access ports into the body cavity to the maximum extent (up to distal ends 37 of arms 36), such that the distance between the user's hand U and the patient's body P is minimized. Such positioning facilitates maximum control of the instrument for ultra-precise manipulation.

Figure 3B:
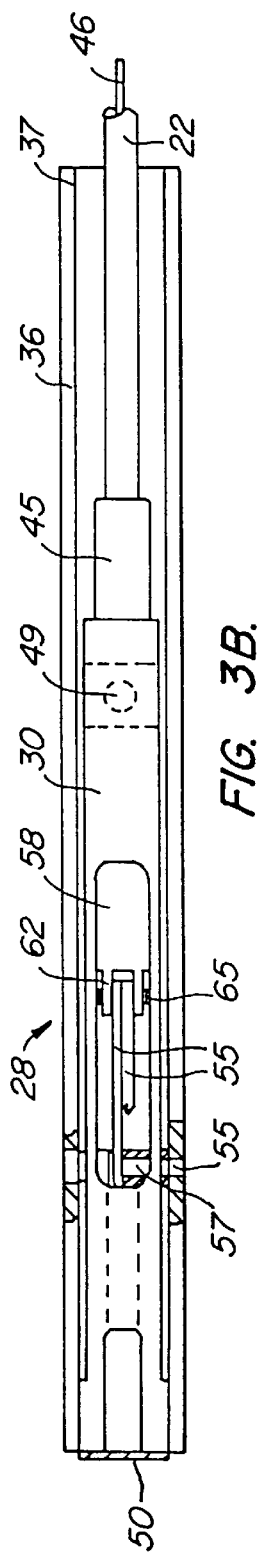
FIGS. 3A–3B are side and top cross-sectional views, respectively, of a second embodiment of an actuator in the microsurgical instrument of FIG. 1.
Figure 3C:
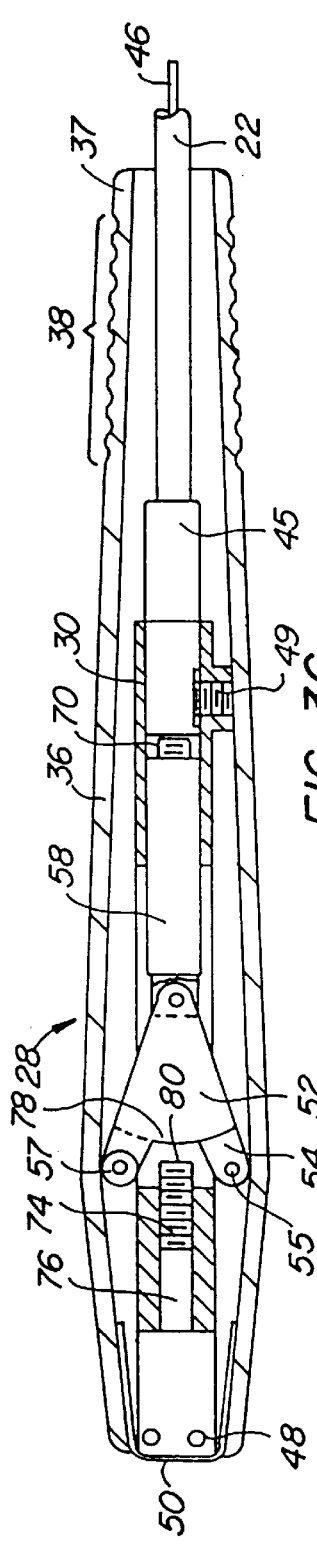
FIG. 3C is a side cross-sectional view of the actuator of FIG. 3A in a closed position.
Figure 3A:
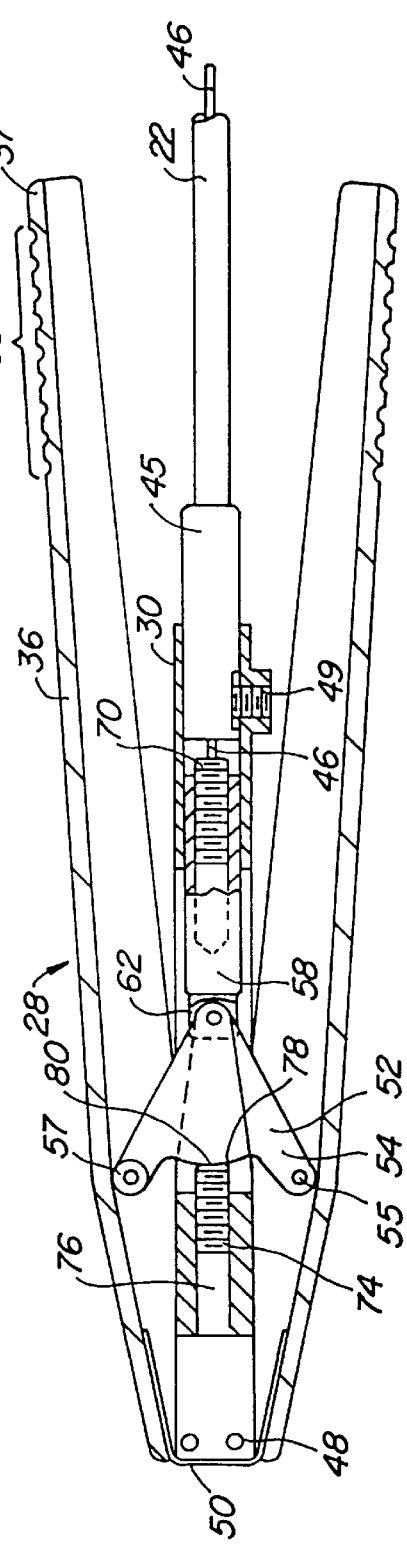

FIGS. 3A–3C illustrate a push-type embodiment of actuator 28 in which inner shaft 46 is configured to be translated distally rather than proximally relative to outer shaft 22 when arms 36 are pivoted inward. The embodiment of FIGS. 3A–3C is in many respects similar to that of FIGS. 2A–2C, except that inner ends 56 of links 52, coupled to proximal end 62 of clevis 58, are disposed distal to outer ends 54, coupled to arms 36. In this way, when arms 36 are pivoted inward, links 52 push clevis 58 and inner shaft 46 distally. To limit the outward travel of arms 36, as well as the proximal movement of inner shaft 46, a limit screw 74 is disposed in a threaded hole 76 in a proximal end of body 30. Links 52 each have an extension 78 on a proximal side thereof configured to engage a distal end 80 of limit screw 74 when arms 36 are in an outward position. The degree of outward travel of arms 36, as well as the axial translation of inner shaft 46, may be adjusted by changing the depth of limit screw 74 within hole 76.

Figure 4A:
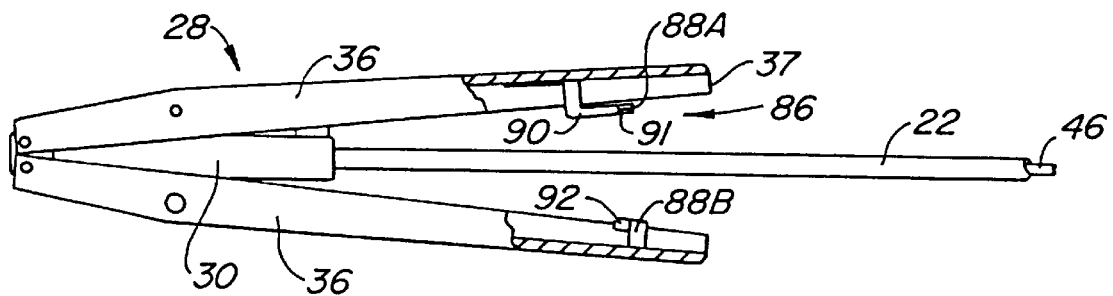
FIGS. 4A–4B are side partial cross-sectional views of an actuator in the microsurgical instrument of FIG. 1 showing two alternative embodiments of an actuator locking mechanism.
Figure 4B:
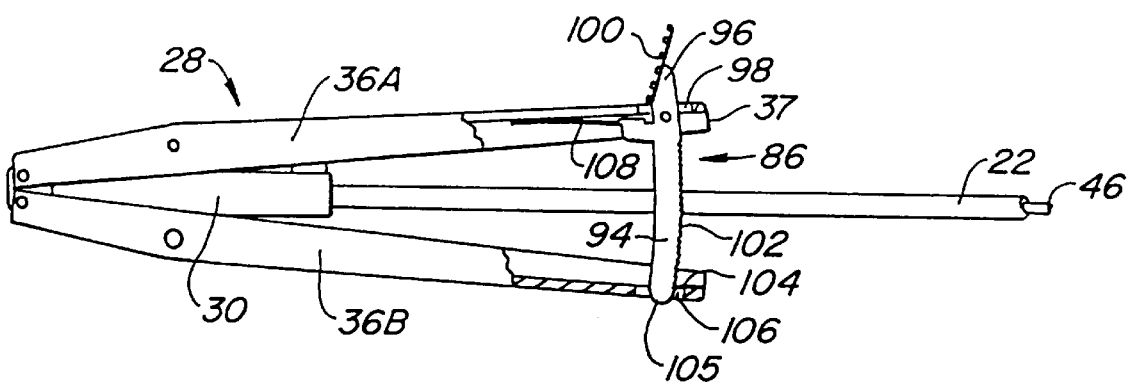

Referring now to FIGS. 4A–4B, actuator 28 may further include locking means 86 for maintaining arms 36 in an inward position when pressure is released therefrom. Locking means 86 may have various configurations, including the single-position design of FIG. 4A, and the ratcheted design of FIG. 4B. In the embodiment of FIG. 4A, locking means 86 comprises a catch 88 attached to each of arms 36 near the distal end 37 thereof. At least a first catch 88A is attached to arm 36 by a resilient, deflectable beam 90, allowing catch 88A to deflect laterally upon engagement with second catch 88B when arms 36 are pressed toward one another. Catch 88A has a stepped portion 91 which is deflected upon contact with the tapered back side of end portion 92. After clearing end portion 92, stepped portion 91 partially recoils from the deflection and resides beneath end portion 92, preventing arms 36 from returning to their outward positions. To release arms 36, they are pressed further inward, whereby catch 88A completely clears end portion 92 of catch 88B and returns to its undetected position. As arms 36 return to their outward positions, the back side of catch 88A slides along the tapered front side of end portion 92.

In the embodiment of FIG. 4B, locking means 86 comprises a ratcheting mechanism to allow arms 36 to be maintained in any of a number of positions between fully open and fully closed. In this embodiment, a rocker arm 94 is pivotally coupled to arm 36A near a distal end 37 thereof. A first end 96 of rocker arm 94 extends through a slot 98 in arm 36, and has a finger pad 100 with grooves or other textural features to reduce slippage when engaged by the user. A plurality of teeth 102 are disposed on a lateral side of rocker aim 94, and are configured to engage a pawl 104 on second arm 36B. A second end 105 of rocker arm 94 extends through a slot 106 in second arm 36B. A biasing means such as a leaf spring 108 is coupled to rocker arm 94 and to arm 36A to urge teeth 102 against pawl 104. In this way, as arms 36 are pressed inward, rocker arm 94 extends through slot 106 and teeth 102 ride sequentially along pawl 104. When arms 36 are in a desired position, pressure may be released and the engagement of pawl 104 against teeth 102 prevents arms 36 from returning outwardly. When arms 36 are to be released, finger pad 100 is pushed distally, pivoting rocker aim 94 in a clockwise direction, and disengaging teeth 102 from pawl 104.

The microsurgical instruments of the invention may have a number of different end-effectors suitable for performing a variety of surgical activities. Several examples of such end-effectors are illustrated in FIGS. 5–10. It will be understood to those of ordinary skill in the art that the principles of the invention may be applied to various end-effector configurations in addition to those illustrated and described specifically here.

The end-effectors in the microsurgical instruments of the invention may be configured for either pull-type or push-type actuation, depending upon whether the pull-type actuator of FIGS. 2A–2C or the push-type actuator of FIGS. 3A–3C is used. An exemplary embodiment of a pull-type end-effector is illustrated in FIG. 5. End-effector 40 comprises a fixed jaw 112 attached to distal end 26 of outer shaft 22, and a movable jaw 114 pivotally coupled to outer shaft 22 or to fixed jaw 112 at a pivot point 115. Inner shaft 46 has a distal end 116 pivotally coupled to a rearward portion 118 of movable jaw 114 proximal to pivot point 115. It is evident that, as inner shaft 46 is translated proximally relative to outer shaft 22, movable jaw 114 pivots toward fixed jaw 112.

An exemplary embodiment of a push-type end-effector is illustrated in FIG. 6. In this embodiment, pivot point 115 is located near a proximal end of movable jaw 114, and inner shaft 46 is coupled to movable jaw 114 distal to pivot point 115. It may be seen that translation of inner shaft 46 distally relative to outer shaft 22 will pivot movable jaw 114 toward fixed jaw 112.

The choice to use either a pull-type end-effector or a push-type end-effector is guided by a variety of considerations, including the geometry of the end-effector, the function which the end-effector is designed to perform, and the preference of the user for either push-type or pull-type actuation. For example, where high forces are needed in the end-effector to perform functions such as gripping or cutting, pull-type actuation is often preferred to eliminate the possibility of buckling in inner shaft 46. In some end-effectors designed for punching or shearing, push-type actuation is often preferred to provide tight, sliding contact between the jaws. In addition, the user may prefer the jaws of the end-effector to be normally closed when arms 36 of actuator 28 are in an outward position, such that the jaws are opened by pressing arms 36 inwardly. In such cases, the instruments of the invention may be easily adapted for either pull-type or push-type actuation by providing the pull to close end-effector of FIG. 5 with the push to close actuator of FIG. 3, or by providing the push to close end-effector of FIG. 6 with the pull to close actuator of FIG. 2.

FIGS. 7–10 illustrate exemplary end-effector configurations suitable for performing various surgical functions. FIGS. 7A–7B illustrate two embodiments of grasping forceps. Both embodiments are useful for a variety of purposes, however, the embodiment of FIG. 7A is particularly useful in mobilizing the internal mammary artery (IMA) for grafting to a coronary artery, as described below. Both embodiments include a fixed jaw 112 and movable jaw 114 have gripping surfaces 120, 122 disposed in opposition to each other so as to come into contact upon closing the jaws. Gripping surfaces 12(0, 122 have textural features such as transverse grooves or teeth 124 to improve grip on tissue or other objects. Various well-known jaw designs may be used, such as DeBakey, Cooley, Mayo, or Babcock. Jaws 112, 114 may be of various sizes and shapes depending upon the particular procedures for which they are adapted. In a particularly preferred embodiment, jaws 112, 114 are adapted for very precise work on extremely small body structures in microsurgeries such as CABG, having a length usually between 3 and 15 mm, preferably between 5 and 10 mm. In the embodiment of FIG. 7A, jaws 112, 114 are disposed at an angle, preferably between about 45° and 90°, relative to the distal direction defined by outer shaft 22, to facilitate grasping the IMA when mobilizing it from the chest wall. In the embodiment of FIG. 7B, jaws 112 are generally orthogonal with outer shaft 22 and are tapered in the distal direction to provide a distal portion of reduced size for enhanced access into small spaces and for use on extremely small structures.

FIG. 8 illustrates a forward-cutting scissors embodiment of end-effector 40. In this embodiment, fixed jaw 112 and movable jaw 114 each have a sharpened cutting edge 126 along an inner side thereof. Movable jaw 114 is configured to pivot alongside fixed jaw 112 such that cutting edges 126 slide along one another in a shearing action. Usually, jaws 112, 114 are tapered to a sharp distal point 128. Preferably, in the scissor embodiment, jaws 112, 114 are again adapted for use in CABG and other microsurgeries, laving a length in the range of 3 to 10 mm, and preferably 3 to 5 mm. Jaws 112, 114 may be disposed at a variety of different angles relative to the distal direction defined by outer shaft 22, from +90° to −90°, depending upon the particular cutting task to be performed.

FIG. 9 illustrates a rearward-cutting scissors embodiment of end-effector 40. In this embodiment, jaws 112, 114 are much like those in the forward-cutting scissors embodiment of FIG. 8, having a sharpened cutting edge 126 and tapering to a distal point 128. However, to facilitate cutting in a proximal direction (toward the user), jaws 112, 114 are disposed at an angle between 90° and 270° relative to the distal direction as defined by outer shaft 22, such that distal points 128 point generally rearward.

FIG. 10 illustrates a suture needle holder embodiment of end-effector 40. In this embodiment, jaws 112, 114 have contact faces 130, 132 disposed in opposition to each other and which engage each other upon closure. Contact faces 130, 132 are adapted for gripping a suture needle tightly between jaws 112, 114 and manipulating the needle for purposes of applying a suture to a body structure. Because such suture needles are typically steel or other hard metal, it is usually desirable to provide an insert 134 of hardened steel, carbide, or other metal on each jaw to enhance grip on the needle and to reduce wear on the gripping surfaces. Contact faces 130, 132 are preferably provided with grooves, diamond knurl patterns, or other textural features to improve grip. In a preferred embodiment, jaws 112, 114 are adapted for holding a BV–1 type suture needle suitable for coronary anastomosis and other microsurgical applications, the jaws usually having a length between 3 and 10 mm, and preferably between 3 and 5 mm. Jaws 112, 114 may also be curved about a transverse axis to facilitate holding a suture needle at various angles relative to shaft 22.

In the embodiments described above, outer shaft 22 remains stationary relative to actuator 28 and inner shaft 46 is translated either distally or proximally relative to outer shaft 22. It should be understood that the instruments of the invention may also be configured so that inner shaft 46 remains stationary relative to actuator 28 and outer shaft 22 is translated relative to inner shaft 46. An example of the latter configuration is illustrated in FIG. 11. Arms 36 are coupled to a body 140, which has an axial bore 141 in which proximal end 142 of inner shaft 46 is fixed. A proximal end 144 of outer shaft 22 is fixed to a sleeve 146 having flats 148 on the lateral sides of a proximal end thereof. A pair of links 150 are coupled at their outer ends 152 to arms 36, and at their inner ends 154 to flats 148 on sleeve 146. As described above, links 150 may be configured to translate outer shaft 22 either distally, as illustrated, or proximally relative to inner shaft 46 by positioning inner ends 154 either distal or proximal relative to outer ends 152.

FIG. 11 further illustrates an exemplary embodiment of an end-effector with which an actuator configured to translate outer shaft 22 is particularly useful. In this embodiment, end-effector 156 comprises a clip applier for applying a surgical clip 158. End-effector 156 may be adapted to apply surgical clips or staples of various types and sizes, including, for example, a Hemoclip® or Atrauclip™ brand surgical clip available from Pilling/Weck of Fort Washington, Pa. Such clips are a titanium or tantalum alloy or pure metal material and have a pair of distally-pointing legs 160 joined together at an apex 162 to form a modified "U" or "V" shape. End-effector 156 includes a pair of jaws 164 adapted to receive clip 158 between them. Jaws 164 extend distally from a bifurcated shank 166 attached to distal end 168 of inner shaft 46. Shank 166 has a straight proximal portion 170 and a flared distal portion 172. As outer shaft 22 translates distally, its distal end 174 engages flared portion 172 of shank 166 and urges jaws 164 toward each other, thereby closing clip 158 held therebetween.

As illustrated in FIG. 12, clip 158 may be positioned about a body structure such as a severed blood vessel BV. Actuator 28 may then be actuated to close clip 158 on blood vessel BV to stop blood flow therethrough. A plurality of clips 158 may be applied to blood vessel BV to isolate a portion of the vessel or to ensure adequate ligation. This technique may be utilized during various surgical procedures including CABG, as described more fully below.

End-effector 156 and clip 158 may have various sizes and shapes, but in a preferred embodiment, are adapted for use in performing CABG and other microsurgeries. In such surgeries, legs 160 of clip 158 may have a length of 2 to 5 mm, preferably 3 to 4 mm, with the distance between legs 160 being 2 to 4 mm. Larger sizes of clips may be employed for larger vessels. End-effector 156 is dimensioned accordingly.

It will be understood to those of ordinary skill in the art that an actuator configured to translate inner shaft 46 relative to a stationary outer shaft 22 may also be adapted to actuate a clip applier like that of FIG. 11. However, it is usually desirable to maintain a constant distance between the user's hand and the body structure to which a clip is to be applied. Therefore, the actuator configuration illustrated in FIG. 11 is generally preferred, since end-effector 156 remains stationary relative to actuator 28 as outer shaft 22 translates distally to close jaws 164.

The method of the invention will now be described with reference to FIGS. 13–17. While a preferred method of performing coronary artery anastomosis in a thoracoscopic CABG procedure will be described in detail here, it should be understood that the principles of the invention may be applied to a wide variety of surgical procedures, both conventional, open procedures as well as minimally-invasive procedures.

Figure 13:
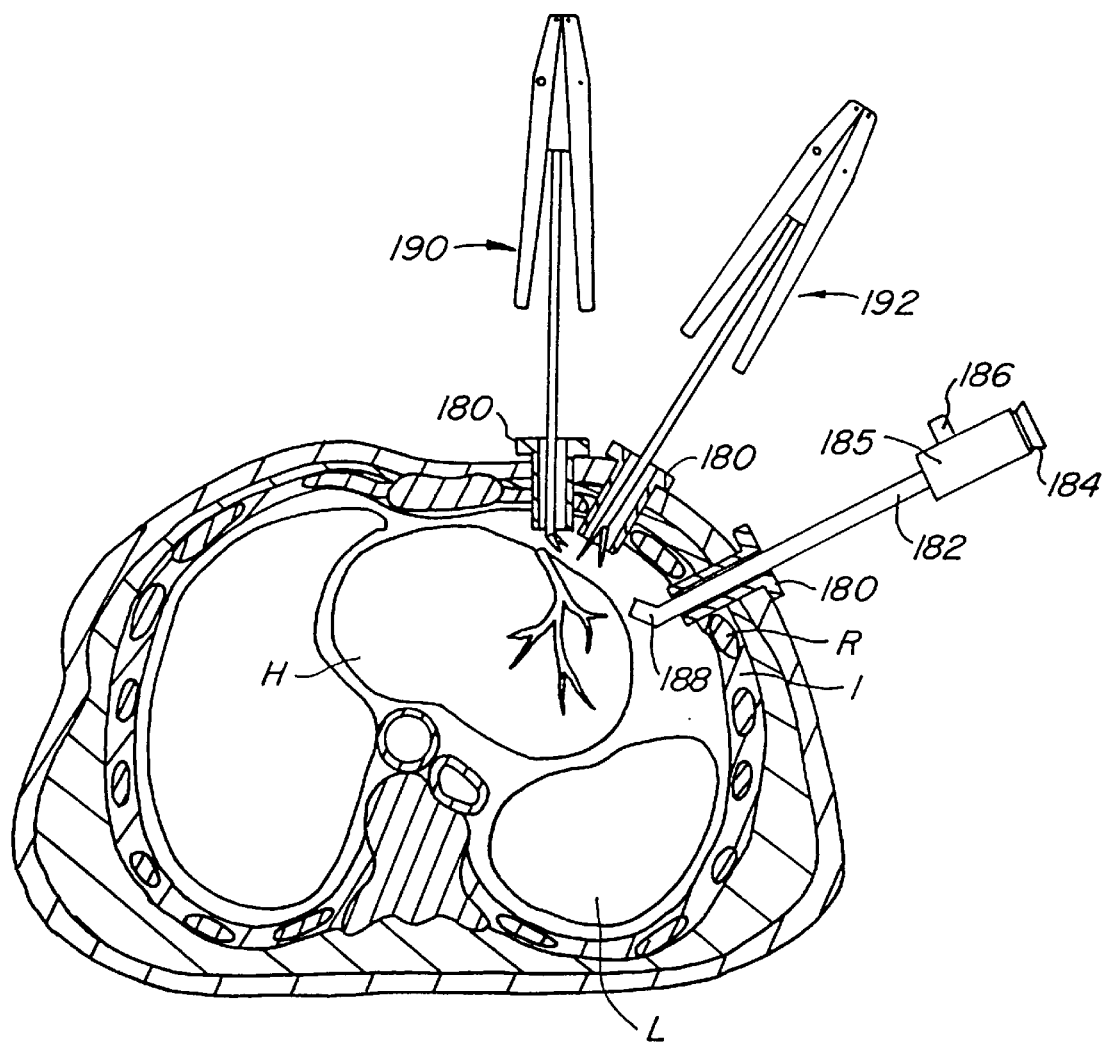
FIG. 13 is a transverse cross-section taken through a patient's thorax inferior to the heart showing the positioning of trocar sleeves and microsurgical instruments according to the method of the invention.

With the patient under general anesthesia, the patient's left lung L is deflated using well-known techniques. Several small incisions are made in the left anterior chest through which trocar sleeves may be positioned to provide access into the thoracic cavity. As illustrated in FIGS. 13, trocar sleeves 180 are positionable within the intercostal spaces I between adjacent ribs R of the rib cage, typically having an outer diameter of less than 12 mm and an inner diameter of 5 to 10 mm. Trocar sleeves 180 thus provide access ports through which the instruments of the invention may be introduced into the thoracic cavity to perform the CABG procedure.

An endoscope 182 is then introduced into the body cavity through a trocar sleeve 180 to facilitate visualization of the thoracic cavity. Endoscope 182 may include an eyepiece 184 for direct visualization of the body cavity, and/or a video camera (not shown) mounted to body 185 for video-based viewing. Distal end 188 of endoscope 182 may be steerable or disposed at an angle to facilitate visualization of the heart H. Endoscope 182 may further include a connector 186 for connecting to a light source (not shown) for transmitting light to distal end 188 for illuminating the thoracic cavity. Endoscope 182 may be a commercially-available endoscope such as the 45° endoscope, available from Olympus, Medical Instruments Division, of Lake Success, N.Y.

The first surgical step to be performed in the CABG procedure is the mobilization of a graft vessel to create a new arterial blood source. Ordinarily, such a graft will be harvested before the patient has been placed on cardiopulmonary bypass and the patient's heart has been stopped. One common type of graft vessel is a vein graft harvested from another part of the patient's body, usually the leg. A second common type of graft vessel is the internal mammary artery (IMA), typically the left IMA (LIMA), in the anterior wall of the patient's chest. Prosthetic grafts may also be used. The IMA is often the preferred form of graft vessel, as it generally maintains patency for a longer period after the CABG procedure, requires less preparation for anastomosis, and is accessible within the thoracic cavity, obviating the need for incisions elsewhere in the body. For these reasons, the use of an IMA graft will be described here, although the techniques described are equally applicable to vein grafts, prosthetic grafts, and other types of grafts.

The IMA must be dissected from its native location in the anterior wall of the thoracic cavity. To accomplish this, a cutting instrument such as an electrocautery tool (not shown), a surgical knife (not shown) or scissors 190, along with grasping forceps 192, are introduced through trocar sleeves 180. The grasping forceps shown in FIG. 7A are usually preferred for this purpose. These instruments may be introduced at various locations, but are usually inserted through trocar sleeves in the right lateral side of the chest to allow the instruments to reach the anterior wall of the thoracic cavity. Using these instruments, a section of the IMA, usually about 10 to 20 cm in length, is cut away from the surrounding tissue with the vessel still intact. Branches of the IMA which are too large to cauterize may be double clipped with small clips and divided between the clips. A clip applier like that illustrated in FIGS. 11–12 may be used for this purpose. A section of the IMA is chosen which, when cut distally, will reach the desired anastomosis site on the LAD. This mobilized section of the IMA must then be isolated to stop blood flow through it. Such isolation may be accomplished by introducing a removable clamp (not shown) into the thoracic cavity and applying the clamp to the IMA near the distal end of the mobilized section but proximal to the point at which the vessel is to be transected. A conventional clamp such as a Fogarty clamp available from Baxter Healthcare Corp. of McGaw Park, Ill. may be used for this purpose. A clip applier, such as that illustrated in FIGS. 11–12, is then introduced into the thoracic cavity and one or more surgical clips are applied to the IMA distal to the point at which it is to be transected. A scissors 190 or other cutting instrument is then used to transect the IMA near the distal end of the mobilized section between the removable clamp and the surgical clips.

The distal end of the mobilized IMA is then prepared for anastomosis. Usually, forceps 192 arc used to withdraw the mobilized section from the thoracic cavity through one of trocar sleeves 180. The distal end is then prepared for anastomosis by cutting away a distal portion of the pedicle surrounding the vessel so that a distal segment of the vessel is exposed. The distal end of the vessel is transected at a non-perpendicular angle suitable for attachment to the LAD in a fishmouth configuration. The vessel may then be returned to the thoracic cavity.

The patient must then be placed on cardiopulmonary bypass, and the heart must be stopped. If the operation is to be performed using minimally-invasive techniques, these must be accomplished without making a sternotomy or other gross thoracotomy in the patient's chest. Minimally-invasive techniques for establishing cardiopulmonary bypass and arresting the health without opening the patient's chest are described in copending application Ser. No. 08/023,778, which has been incorporated herein by reference, as well as in copending applications Ser. No. 07/991,188, filed Dec. 15, 1992, and Ser. No. 8/123,411, filed Sep. 17, 1993, which are both hereby incorporated herein by reference in their entirety.

Figure 14:
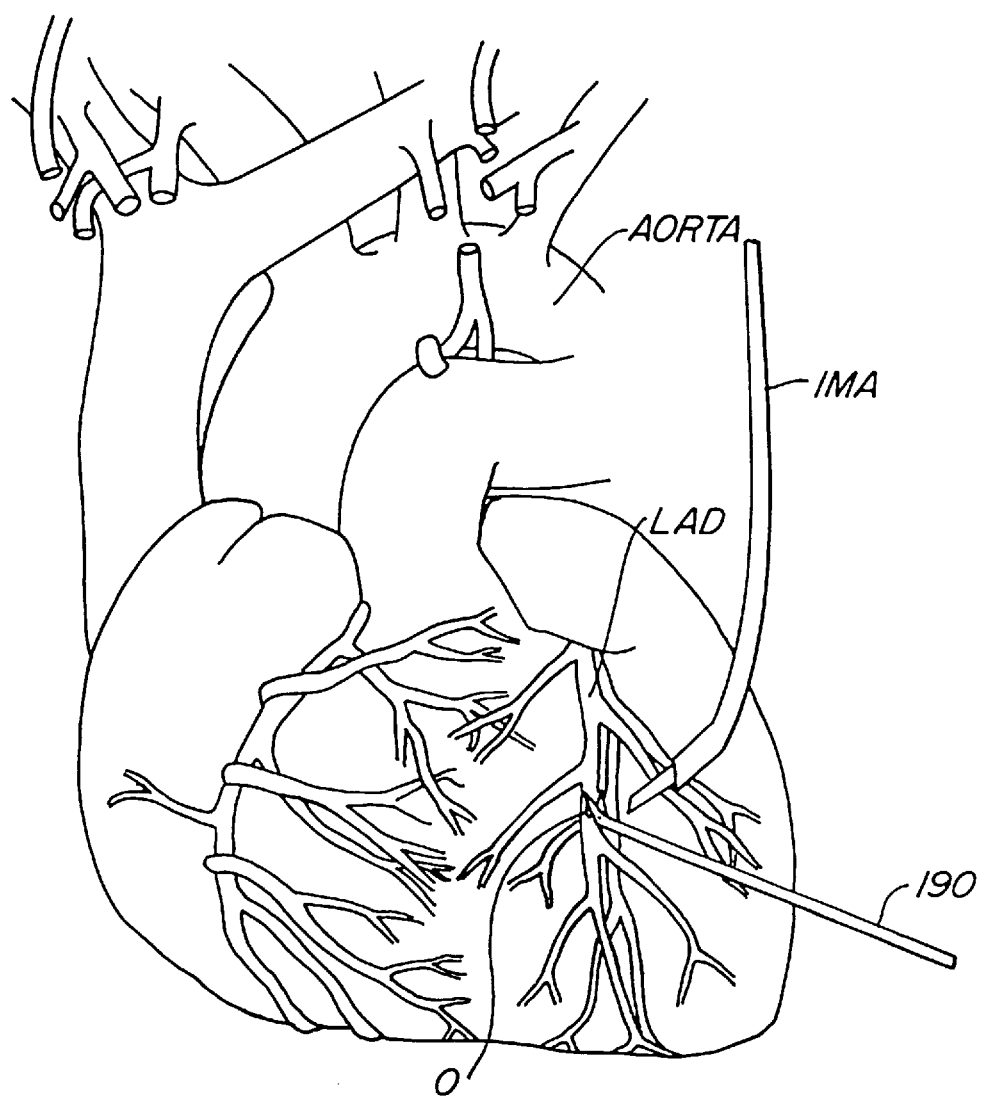
FIGS. 14–15 and 17 are anterior elevational views of a patient's heart, illustrating the performance of a coronary artery anastomosis according to the method of the invention.

Once the heart has been stopped and the patient is supported on cardiopulmonary bypass, the anastomosis of the IMA to the LAD may be performed. As illustrated in FIG. 14, an opening O is formed in the LAD at the desired location of the anastomosis, distal to the lesion which is to be bypassed. A scissors 190 or other cutting instrument is introduced through a trocar sleeve 180 and a small incision is formed in the LAD, usually about 2 to 5 mm in length. The rearward cutting scissors illustrated in FIG. 9 may also be useful for this purpose, depending upon the orientation of the heart and/or LAD relative to the user and relative to the trocar sleeve through which the instrument is introduced.

It may be necessary, either before or after an opening is formed in the LAD, to dissect a small section of the LAD on either side of the anastomosis site away from the epicardium to obtain better access for performing an anastomosis. Scissors 190 or other cutting instruments may be used for this purpose. The dissected section of the LAD may be retracted away from the surface of the heart using conventional means such as Retract-O-Tape Vascular Loops available from Quest Medical of Dallas, Tex.

Figure 15:
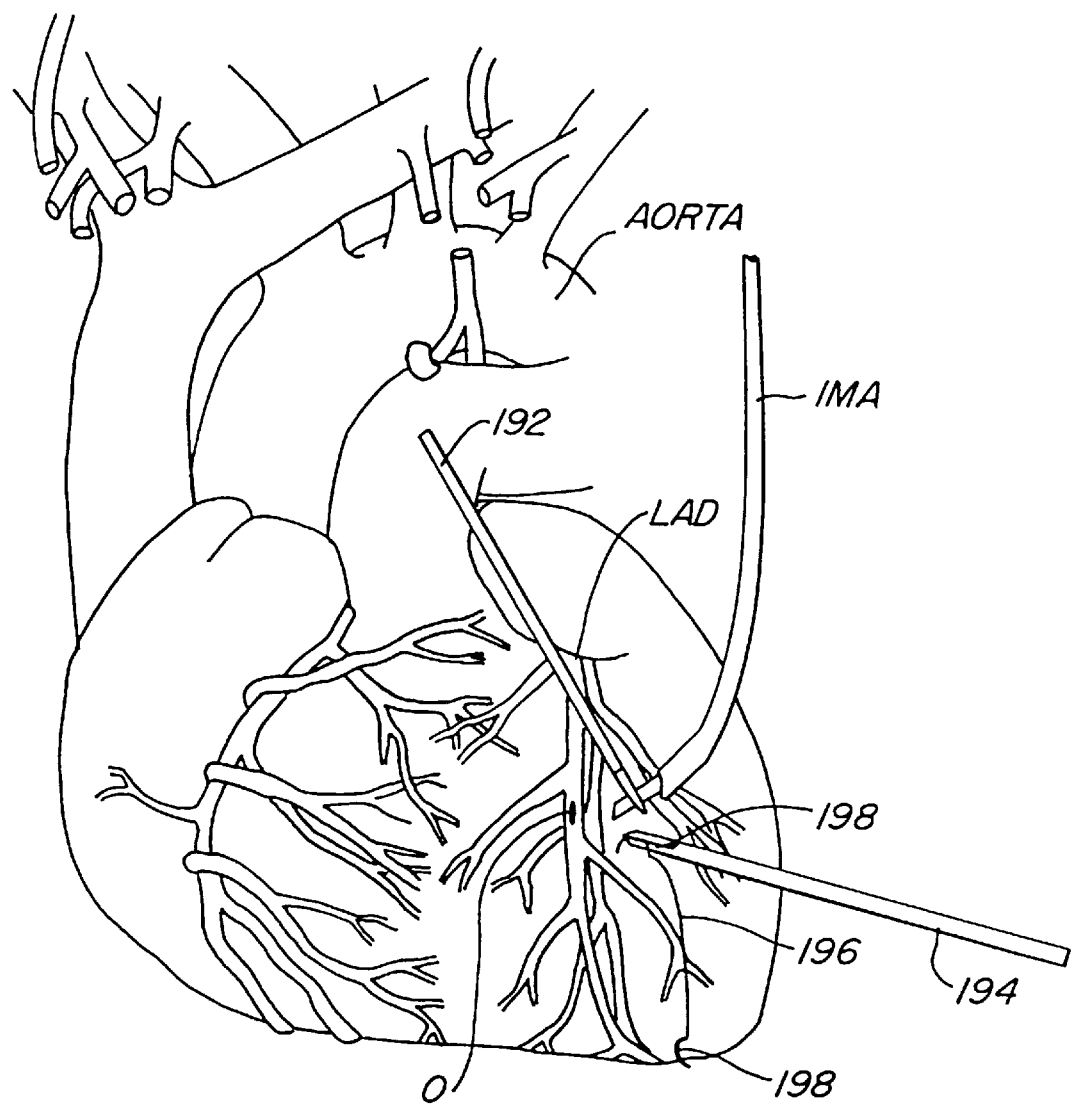
Figure 16A:
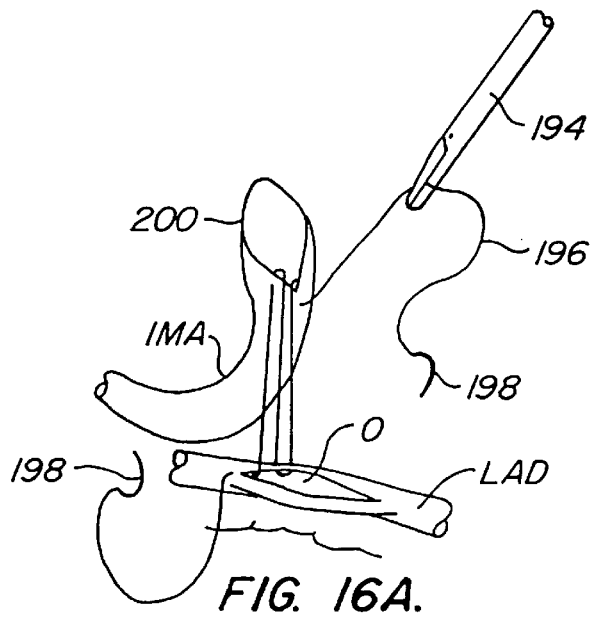
FIGS. 16A–16E illustrate a method of suturing a graft vessel to a coronary artery according to the method of the invention.
Figure 16B:
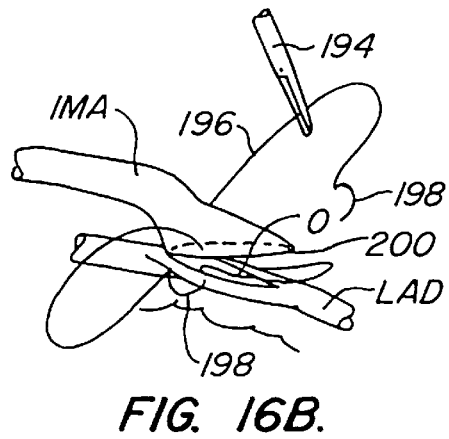
Figure 16D:
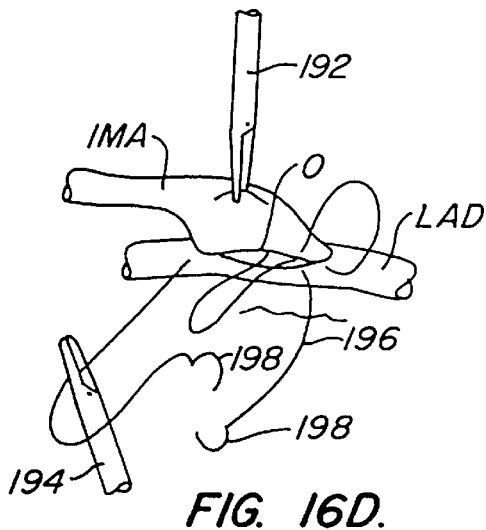
Figure 16C:
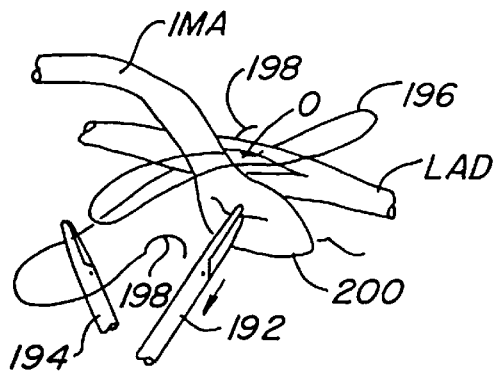
Figure 16E:
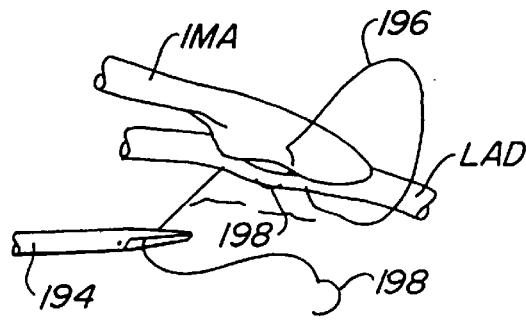

To perform the anastomosis, the IMA is sutured to the LAD over opening O. As illustrated in FIG. 15, a grasping instrument such as forceps 192 is introduced through a trocar sleeve for holding the IMA in position during the anastomosis. One or more needle drivers 194 are also introduced into the thoracic cavity, as well as a suture 196, usually having needles 198 on both ends. Needle drivers 194 are used to manipulate needles 198 so as to suture the distal end of the IMA to the LAD, under visualization by means of endoscope 182 (FIG. 13) or other visualization device.

Figure 17:
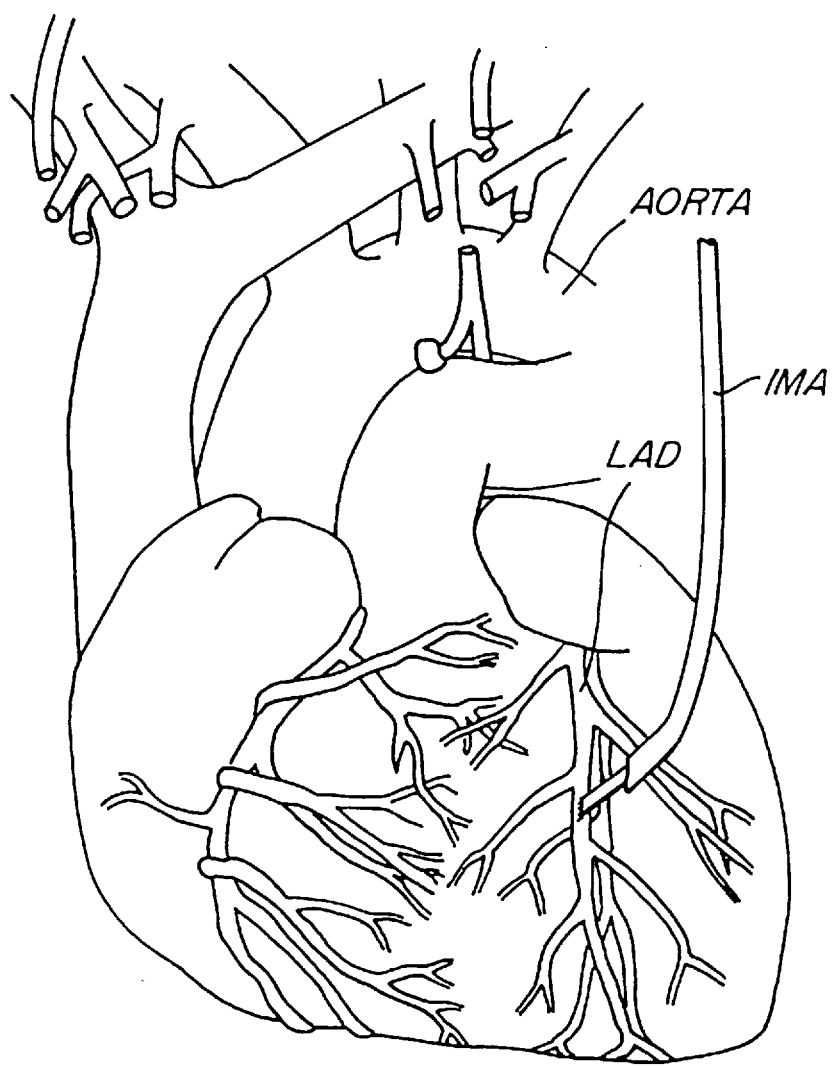

Various techniques may be used for suturing the IMA to the LAD. An exemplary technique is illustrated in FIGS. 16A–16E and is described comprehensively in Kirklin and Barratt-Boyes, *Cardiac Surgery*, pp. 207–277(1986), the disclosure of which is incorporated herein by reference. At least one pair of needle drivers 194 are required, along with a grasping instrument such as forceps 192. It may be seen from the illustrations that the suture is passed sequentially through the wall of the LAD around the edges of opening O and through the wall of the IMA around its distal end 200. This is repeated until suture loops have been made about the entire circumference of the IMA spaced approximately 0.3 mm apart The loops are drawn tight and the suture is tied off in a conventional manner to provide a secure and fluidly sealed attachment of the IMA to the LAD, as illustrated in FIG. 17. The removable clip (described above) is then removed from the IMA, allowing blood to flow through the IMA and into the LAD after the heart has been restarted.

When the anastomosis has been completed, the patients heart is restarted and cardiopulmonary bypass is discontinued. All trocar sleeves and cannulas are removed from the patient, and the thoracic incisions and arterial and venous punctures are closed. The patient is then recovered from anesthesia.

The microsurgical instruments of the invention are specially adapted to facilitate the ultra-precise microsurgical steps of thoracoscopic CABG. The IMA, LAD, and other body structures manipulated during the CABG procedure are extremely small, with diameters in the range of 1 to 4 mm, and are relatively fragile structures which must be handled gently and precisely. The microsurgical forceps, scissors, needle drivers, and clip appliers of the invention are well-suited to grasping these structures, making the necessary transections, incisions, and ligations, and applying extremely small sutures, allowing anastomoses to be performed accurately, efficiently, repeatably, and with minimal trauma. The instruments of the invention not only have the very small dimensions necessary for such microsurgery, but the means of holding and actuating these instruments allow extremely precise actuation and control of the end-effectors. Moreover, the elongated, low-profile configuration, high stiffness, and optimal end-effector geometries of these instruments facilitate the performance of CABG and other operations through small incisions or trocar sleeves rather than through the gross, open thoracotomies used in conventional open-heart surgery.

While the above is a complete description of the preferred embodiments of the invention, various alternatives, modifications and equivalents may be used. Therefore, the above description should not be taken as limiting the scope of the invention, which is defined by appended claims.

What is claimed is:

1. A surgical instrument comprising:
   an outer shaft;
   an inner shaft generally parallel to the outer shaft and movable relative thereto;
   an actuator body attached to a first shaft selected from the outer shaft and the inner shaft;
   a first arm linked to a second shaft selected from the outer shaft and the inner shaft and having a proximal end and a distal end, the proximal end being pivotally coupled to the actuator body and the distal end extending distally and outwardly from the actuator body on a first lateral side of the outer shaft to form an acute angle therewith;
   a second arm linked to the second shaft and having a proximal end and a distal end, the proximal end being pivotally coupled to the actuator body, and the distal end extending distally and outwardly from the actuator body on a second lateral side of the outer shaft opposite the first lateral side to form an acute angle therewith, the distal ends of the first and second arms being pivotable between an open position away from each other and a closed position closer to each other so as to move the inner shaft relative to the outer shaft; and
   a locking mechanism coupled to the first arm and configured to engage the second arm in the closed position to retain the first and second arms in the closed position.

2. The surgical instrument of claim 1 wherein the locking mechanism comprises a beam having a first end attached to the first arm and a second end extending inwardly toward the second arm, the second end being deflectable and having a catch thereon for engaging the second arm in the closed position.

3. The surgical instrument of claim 2 further comprising a step mounted to the second arm for engaging the catch in the closed position.

4. The surgical instrument of claim 2 wherein the catch is configured to release the second arm upon pushing the first arm toward the second arm from the closed position.

5. The surgical instrument of claim 4 wherein the catch is in a detected configuration when engaging the step in the closed position.

6. The surgical instrument of claim 5 wherein the catch is configured to recoil to an unbiased configuration upon pushing the first arm toward the second arm from the closed position, the catch being configured to avoid engagement with the step in the unbiased configuration as the first and second arms return to the open position.

7. The surgical instrument of claim 1 wherein the locking mechanism comprises a ratchet for releasably locking the first arm relative to the second arm in a plurality of positions between the open and closed positions.

8. The surgical instrument of claim 7 wherein the ratchet comprises a rocker arm coupled to the first arm and having a plurality of teeth along an edge thereof, and a pawl on the second arm for sequentially engaging the teeth as the first arm is moved toward the second arm.

9. The surgical instrument of claim 7 wherein the rocker arm is pivotably mounted to the first arm and biased in a first direction such that the teeth are urged against the pawl.

10. The surgical instrument of claim 1 further comprising an end-effector coupled to the outer shaft and coupled to the inner shaft so as to move in response to movement of the inner shaft relative to the outer shaft.

11. The surgical instrument of claim 10 wherein the end effector comprises a first jaw coupled to the outer shaft and a second jaw coupled to the inner shaft, the second jaw being movable relative to the first jaw.

12. The surgical instrument of claim 11 wherein the second jaw is pivotably coupled to the first jaw.

13. The surgical instrument of claim 12 wherein the first and second jaws have opposing faces for clamping an object therebetween upon closure of the jaws.

14. The surgical instrument of claim 12 wherein the first and second jaws have cutting edges movable in a shearing relationship as the jaws are closed.

15. The surgical instrument of claim 1 further comprising a spring for biasing the first and second arms into the open position.

16. A surgical instrument comprising:

an outer shaft;

an inner shaft generally parallel to the outer sly and movable relative thereto;

an actuator body attached to a first shaft selected from the outer shaft and the inner shaft;

a first arm linked to a second shaft selected from the outer shaft and the inner shaft and having a proximal end and a distal end, the proximal end being pivotally coupled to the actuator body and the distal end extending distally and outwardly from the actuator body on a first lateral side of the outer shaft to form an acute angle therewith;

a second arm linked to the second shaft and having a proximal end and a distal end, the proximal end being pivotally coupled to the actuator body, and the distal end extending distally and outwardly from the actuator body on a second lateral side of the outer shaft opposite the first lateral side to form an acute angle therewith, the distal ends of the first and second arms being pivotable between an open position away from each other and a closed position closer to each other so as to move the inner shaft relative to the outer shaft; and a flat spring having a first end engaging an inner surface of the first arm and a second end engaging an inner surface of the second arm for biasing the first and second arms into the open position.

17. The surgical instrument of claim 16 wherein the flat spring is generally U-shaped when engaging the first and second arms and is biased toward a flat configuration.

18. The surgical instrument of claim 17 wherein the flat spring has a first end segment disposed along an inner surface of the first and second end segment disposed along an inner surface of the second arm, and a connecting segment between the first and second end segments, the connecting segment being disposed between the proximal ends of the first and second arms.

19. A surgical instrument comprising:

an outer shaft;

an inner shaft generally parallel to the outer shaft and movable relative thereto;

an actuator body attached to a first shaft selected from the outer shaft and the inner shaft, the actuator body having a longitudinal channel therein;

a clevis slidably positioned in the longitudinal channel and attached to a second shaft selected from the outer shaft and the inner shaft;

a first arm linked to the clevis and having proximal and distal ends, the proximal end being pivotally coupled to the actuator body and the distal end extending distally and outwardly from the actuator body on a first lateral side of the outer shaft to form an acute angle therewith;

a second arm linked to the clevis and having proximal and distal ends, the proximal end being pivotally coupled to the actuator body, and the distal end extending distally and outwardly from the actuator body on a second lateral side of the outer shaft opposite the first lateral side to form an acute angle therewith, the distal ends of the first and second arms being pivotable between an open position away from each other and a closed position closer to each other so as to slide the clevis within the longitudinal channel, thereby moving the inner shaft relative to the outer shaft.

20. The surgical instrument of claim 19 wherein the first arm is linked to the clevis by a first link having a first end pivotably coupled to the first arm and a second end pivotably coupled to the clevis and wherein the second arm is linked to the clevis by a second link having a first end pivotably coupled to the second arm and a second end pivotably coupled to the clevis.

* * * * *